US00PP29285P2

(12) United States Plant Patent
Scheys

(10) Patent No.: US PP29,285 P2
(45) Date of Patent: May 8, 2018

(54) ×*HEUCHERELLA* PLANT NAMED 'ART NOUVEAU'

(50) Latin Name: ×*Heucherella* hybrid
Varietal Denomination: Art Nouveau

(71) Applicant: Diederik Alexander Maria Scheys, Réty (FR)

(72) Inventor: Diederik Alexander Maria Scheys, Réty (FR)

( * ) Notice: Subject to any disclaimer, the term of this patent is extended or adjusted under 35 U.S.C. 154(b) by 0 days. days.

(21) Appl. No.: 15/330,012

(22) Filed: Jul. 25, 2016

(51) Int. Cl.
*A01H 5/12* (2018.01)

(52) U.S. Cl.
USPC ..... Plt./441

(58) Field of Classification Search
USPC ..... Plt./441, 440, 486
CPC ..... A01H 5/12; A01H 5/02; A01H 5/00
See application file for complete search history.

(56) References Cited

PUBLICATIONS

Plantagogo Catalogue retrieved on Aug. 22, 2017, retrieved from the Internet at https://www.plantagogo.com/catalog/PlantagogoCatalogue.pdf, pp. 1-2, 21, 36, 40.*

* cited by examiner

*Primary Examiner* — June Hwu
(74) *Attorney, Agent, or Firm* — Penny J. Aguirre

(57) ABSTRACT

A new cultivar of ×*Heucherella* named 'Art Nouveau', that is characterized by its a vigorous growth habit, its leaf coloration that is dark green with a conspicuous large dark brown coloration in the centers, its long blooming habit; blooming late spring to late summer in Belgium, and its flowers that are white in color on tall flowering stems.

2 Drawing Sheets

Botanical classification: ×*Heucherella* hybrid.
Cultivar designation: 'Art Nouveau'.

BACKGROUND OF THE INVENTION

The present invention relates to a new and distinct cultivar of ×*Heucherella* and is hereinafter referred to by its cultivar name 'Art Nouveau'.

The new cultivar was derived from a controlled breeding program conducted by the Inventor in Pellenberg, Belgium with the objective of creating new cultivars of ×*Heucherella* that exhibit strong, healthy and vigorous plant habits. The Inventor made a cross in May of 2007 between an unnamed and unpatented plant of *Heuchera*×*villosa* as the female parent and an unnamed and unpatented plant of a *Tiarella* of hybrid origin as the male parent. The Inventor selected 'Art Nouveau' in August of 2008 as a single unique plant amongst the seedlings that resulted from the above cross.

Asexual propagation of the new cultivar was first accomplished by tissue culture using meristem tissue under the direction of the Inventor in Beervelde, Belgium in August of 2008. Asexual propagation of the new cultivar by tissue culture has shown that the unique features are stable and reproduced true to type in successive generations.

SUMMARY OF THE INVENTION

The following traits have been repeatedly observed and represent the characteristics of the new cultivar. These attributes in combination distinguish 'Art Nouveau' as a new and unique cultivar of ×*Heucherella*.

1. 'Art Nouveau' exhibits a vigorous growth habit.
2. 'Art Nouveau' exhibits leaf coloration that is dark green with a conspicuous large dark brown coloration in the centers.
3. 'Art Nouveau' exhibits a long blooming habit; blooming late spring to late summer in Belgium.
4. 'Art Nouveau' exhibits flowers that are white in color on tall flowering stems.

The female parent differs from 'Art Nouveau' in having leaves that are green in color, leaf margins that are less incised, a blooming period in autumn and a plant habit that is less dense. The male parent differs from 'Art Nouveau' in having leaf margins that are less incised, a blooming period in late spring and summer and flower panicles that are much shorter in height and denser. 'Art Nouveau' can be most closely compared to ×*Heucherella* cultivars 'Spotlight' (U.S. Plant Pat. No. 16,835) and 'Kimono' (U.S. Plant Pat. No. 12,154). Both are similar to 'Art Nouveau' in having leaves that are green with dark centers in color. 'Spotlight' differs from 'Art Nouveau' in having a shorter plant height, a less vigorous growth habit, a plant habit that is less dense and less sun resistance. 'Kimono' differs from 'Art Nouveau' in having leaf margins that are less incised, a shorter plant height, a less vigorous growth habit and less sun resistance.

BRIEF DESCRIPTION OF THE DRAWING

The accompanying colored photographs illustrate the overall appearance and distinct characteristics of the new ×*Heucherella*. The photographs were taken of a 2 year-old plant as field grown in a polyethylene tunnel in Pellenberg, Belgium and placed in a container in for the photographs.

Figure 2:
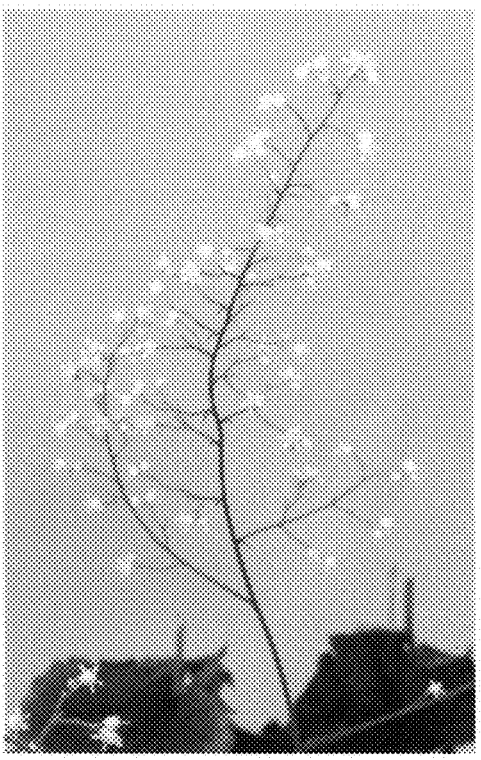

The photograph in FIG. 2 provides a close-up view of the inflorescence of 'Art Nouveau'.

Figure 3:
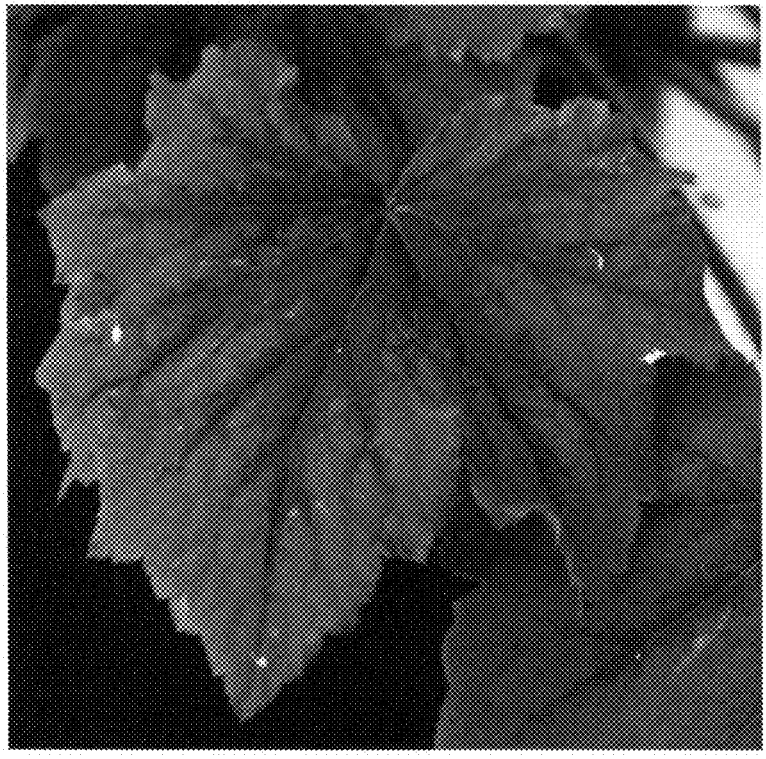

FIG. 3 provides a close-up of a leaf of 'Art Nouveau'.

Figure 1:
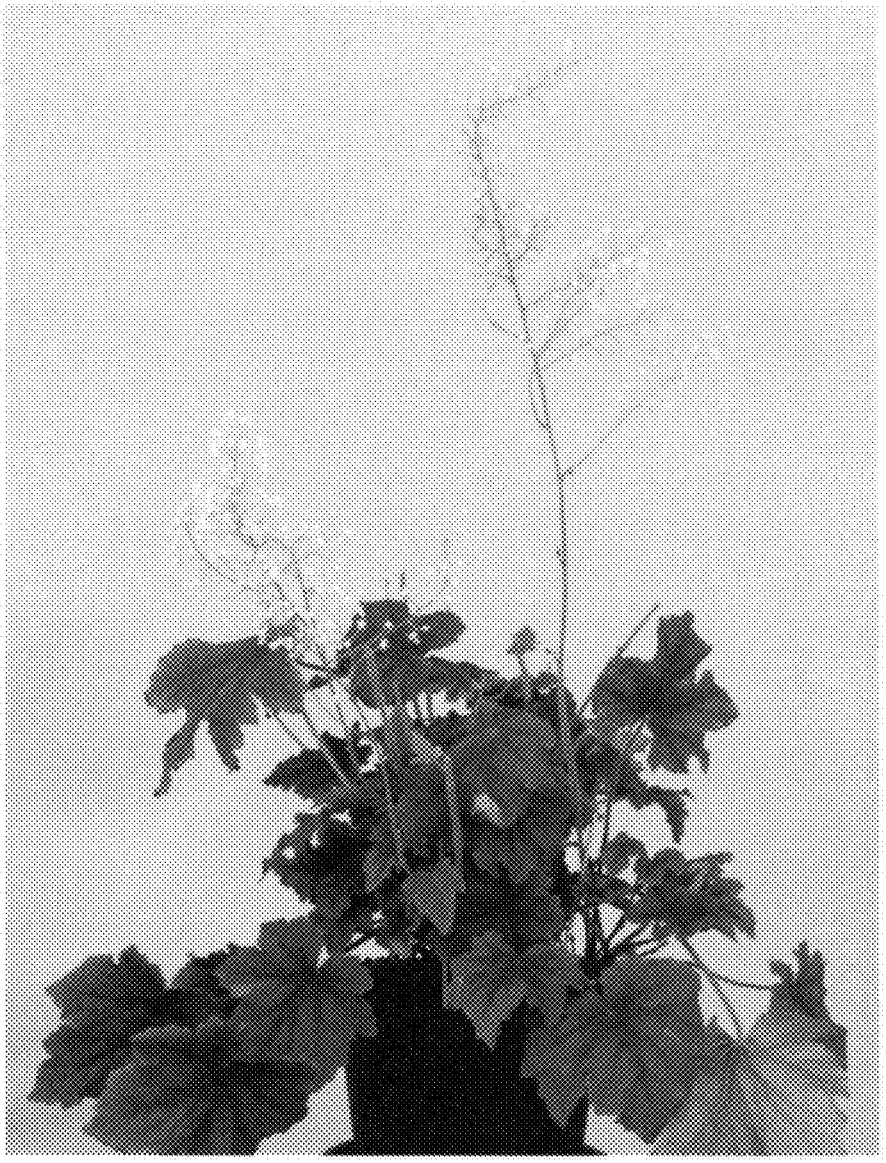
FIG. 1 provides a side view of 'Art Nouveau' in bloom.

The greyed-orange coloration on the leaf margins in FIG. 1 and FIG. 3 are due to growing in dry conditions and is not a characteristic of the claimed plant.

The colors in the photographs are as close as possible with the photographic and printing technology utilized and the color values cited in the Detailed Botanical Description accurately describe the colors of the new ×*Heucherella*.

DETAILED BOTANICAL DESCRIPTION OF THE PLANT

The following is a detailed description of 2 year-old plants as field grown in a polyethylene tunnel in Pellenberg, Belgium. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period.*—Late spring to late summer in Belgium.

*Plant type.*—Herbaceous perennial.

*Plant habit.*—Compact, clump-forming, flattened mounded foliage.

*Height and spread.*—Average of 31.8 cm in length from the soil to top of leaves, 90 cm in length from the soil to the top of the inflorescences and 65 cm in width.

*Hardiness.*—At least in U.S.D.A. Zones 3 to 9.

*Diseases and pests.*—Not susceptibility or resistance to pests and diseases has been observed.

*Root description.*—Fibrous roots on woody rootstalks, 199B in color.

*Branching habit.*—Basal rosettes of leaves on petioles.

*Propagation.*—Tissue Culture.

*Root development.*—An average of 20 weeks to fully develop in a 9-cm container from a tissue culture plug.

*Growth rate.*—Moderate to vigorous.

Foliage description:

*Leaf shape.*—Broad ovate to near orbicular.

*Leaf division.*—Simple.

*Leaf base.*—Hastate-cordate.

*Leaf apex.*—Acute.

*Leaf venation.*—Laciniate, upper vein color 146B to 146C, lower vein color 144B.

*Leaf margins.*—Moderately lobed with an average of 7 lobes per leaf, crenate with mucronate tips.

*Leaf attachment.*—Petiolate.

*Leaf arrangement.*—Alternate in basal rosettes.

*Leaf surface.*—Upper surface; matte, lower surface; slightly glossy, both surfaces densely covered with short strigose hairs, average of 0.15 mm in length and 156D in color.

*Leaf color.*—Young upper surface; 200A to 200B, irregularly margined 143A to 143B, young lower surface; N200A to N200B, irregularly margined 143C, mature upper surface; 137B, around main and secondary veins 202A, mature lower surface; between 146B and 147B, around main and secondary veins 201A to 201B.

*Leaf size.*—An average of 17.4 cm in length and 16.5 cm in width.

*Leaf quantity.*—Average of 23 per rosette.

*Petioles.*—Round in shape, an average of 25.1 cm in length, 3.5 cm in width, upper surface color 148A, lower surface color between 144A and 146B, both surfaces densely pubescent.

*Stipules.*—At the base of each leaf, average of 1.7 cm in length, 5 mm in width, narrow acute tip, 183D in color, densely covered with short strigose hairs 4 mm in length and 156D in color.

Flower description:

*Inflorescence type.*—Compound spike.

*Inflorescence size.*—Reaches an average of 45.5 cm in height and 14.6 cm in width.

*Inflorescence no.*—An average of 8.

*Flower fragrance.*—None.

*Flower quantity.*—Average of 500 flowers per inflorescence.

*Flower lastingness.*—Average of 7 days per flower, flowers self cleaning.

*Flower buds.*—Ovate in shape, average of 2 mm in diameter and 3 mm in depth, color; 155D, base 150D.

*Flower aspect.*—Outward to slightly drooping.

*Flower shape.*—Campanulate.

*Flower size.*—Average of 6 mm in length and 8 mm in diameter.

*Petals.*—About 5, narrowly elliptic to oblanceolate in shape and emerge from between sepals in hypanthium, margin is entire, apex is narrowly acute, about 4 mm in length and 1 mm in width, upper and lower surface smooth and matte, color of upper and lower surface when opening and fully opened is NN155D.

*Calyx.*—Campanulate, sepals fused at base to hypanthium, 4.5 mm in length, 3.5 mm in diameter.

*Sepals.*—5, campanulate hypanthium, elliptic shape, average of 4.5 mm in length and 2 mm in width, margin is entire, apex is broadly acute, based is fused, young and mature upper surface color; NN155C, tips 145D, young and mature lower surface color; NN155C, lower half strongly tinged N170D, tip 145D, surfaces are both matte, lower side densely covered with short glandular hairs 0.2 mm in length and match sepal surface.

*Peduncle.*—Primary; average of 79.1 cm in length and 2.5 mm in diameter, 144C in color, surface pubescent, held at an average angle of 45°, moderate strength, secondary; average of 10.2 cm in length, 1 mm in diameter, held at an average angle of 60°, 144C in color, surface pubescent, moderate strength.

*Pedicel.*—Average of 3 mm in length and 0.5 mm in diameter, surface densely pubescent, moderately strong, held straight on top, 144D in color.

*Gynoecium.*—Pistils; 2, 3 mm in length, club-shaped, stigmas; pointed in shape, NN155D in color, styles; 2.75 mm in length and NN155D in color, ovary; NN155C in color.

*Androecium.*—Stamens; 5, anthers; ovate in shape, about 0.3 mm in length and 167D in color, filaments; 3 mm in length and NN155C in color, pollen quantity is low and 156D in color.

*Seed.*—Seed development of the new cultivar has not been observed to date.

It is claimed:

1. A new and distinct cultivar of ×*Heucherella* plant named 'Art Nouveau' as herein illustrated and described.

* * * * *